United States Patent [19]
Giurtino et al.

[11] Patent Number: 5,615,690
[45] Date of Patent: Apr. 1, 1997

[54] TISSUE CORE BIOPSY CANNULA

[75] Inventors: Joel F. Giurtino; David Turkel, both of Miami, Fla.; David P. Gordon, Stamford, Conn.

[73] Assignee: Symbiosis Corporation, Miami, Fla.

[21] Appl. No.: 389,757

[22] Filed: Feb. 15, 1995

[51] Int. Cl.$^6$ ................................................ A61B 10/00
[52] U.S. Cl. ........................................................ 128/754
[58] Field of Search ........................... 128/749, 751–754; 606/167, 170

[56] References Cited

U.S. PATENT DOCUMENTS

| | | | |
|---|---|---|---|
| 4,708,147 | 11/1987 | Haaga | 128/754 |
| 5,199,441 | 4/1993 | Hogle | 128/753 |

FOREIGN PATENT DOCUMENTS

| | | | |
|---|---|---|---|
| 0221007 | 6/1987 | European Pat. Off. | 128/754 |
| 1553086 | 3/1990 | U.S.S.R. | 128/754 |
| 8203167 | 9/1982 | WIPO | 128/754 |

Primary Examiner—Max Hindenburg
Attorney, Agent, or Firm—David P. Gordon

[57] ABSTRACT

A tissue core biopsy cannula of the present invention includes a distal end which is ground in two planes which intersect each other at a first angle along a line which intersects the longitudinal axis of the cannula at a second angle. This produces a cardioid shaped opening in the distal end of the cannula. The entire edge of the sidewall is thereby inclined inward toward the distal opening and two distal cutting edges are provided. According to the presently preferred embodiment, the first angle at which the two planes intersect is approximately 60° and the second angle at which the intersection of the two planes intersects the longitudinal axis of the cannula is approximately 20°. In order to aid in removal of the biopsy sample from the target tissue site, the cannula according to the invention is provided with side fenestration holes and/or a split end which aids in grasping the tissue so that it can be pulled away from the target tissue site. The cannula according to the invention may be used with a solid stylet or a notched stylet and may be provided as part of a manual or automatic biopsy tool. A preferred stylet for use with the cannula has a distal end which is also ground in two planes like the distal end of the cannula.

20 Claims, 5 Drawing Sheets

TISSUE CORE BIOPSY CANNULA

BACKGROUND OF THE INVENTION

1. Field of the Invention

The invention relates to tissue core biopsy instruments. More particularly, the invention relates to a tissue core biopsy cannula having an improved geometry at its needle point.

2. State of the Art

The biopsy procedure involves the diagnostic evaluation of sample cells which are removed from a patient. There are many different types of instruments used to obtain sample cells for analysis. One common instrument which is used to obtain soft tissue samples is a coring cannula having a needle point. The coring cannula may be manually operated or may be attached to a mechanical device which permits semi-automatic operation. In either case, the geometry of the cannula and its needle point are functionally the same. In operation, the coring cannula is typically fitted with a stylet which substantially occludes the hollow interior of the coring cannula. The stylet is usually provided with a sharpened distal end which facilitates insertion of the cannula-stylet assembly into the body. The stylet prevents unwanted tissue from entering the cannula while the cannula is moved through the body to the target tissue.

According to one type of biopsy instrument, the stylet is provided with a sampling notch proximal of its sharpened point. Once the cannula-stylet assembly has reached the target tissue, the stylet is moved distally out of the cannula exposing the sampling notch to the target tissue. A portion of target tissue prolapses and fills the region defined by the notch in the stylet. The cannula is then moved distally over the notch in the stylet, severing the sample and capturing it. The cannula-stylet assembly is then removed from the body with the sample securely held inside the cannula. While effective, this type of biopsy instrument only permits a relatively small sample to be taken, limited in size by the length and depth of the notch.

Another type of biopsy instrument includes a solid stylet. When the cannula-stylet assembly has reached the target tissue, the stylet is withdrawn from the cannula. The cannula is then advanced into the target tissue so that its needle point cuts the target tissue and a relatively large core sample of the target tissue is captured in the hollow interior of the cannula. If successful, the core sample is still connected to adjacent target tissue distal of the needle point of the cannula, however. If the cannula is merely withdrawn from the target tissue, it is possible that the core sample will remain connected to the adjacent target tissue and will evade capture by the cannula.

Several methods are used to prevent the core sample from exiting the cannula. One method is to apply negative pressure at the proximal end of the cannula while withdrawing the cannula from the target tissue. Another method is to provide the cannula with a non-cylindrical lumen such that when the cannula is rotated, the captured tissue is rotated relative to the adjacent tissue to sever the sample from the adjacent tissue.

While it is important to take measures to keep the sample in the cannula while the cannula is withdrawn, it is equally important to assure that the sample is actually captured by the cannula. The cannulae used in tissue core biopsy instruments are typically relatively small, having a diameter in the range of one-half to six millimeters. Clearly, the smaller the cannula diameter, the less disruptive the biopsy procedure will be. However, when the cannula diameter is small, there is the possibility that tissue will spread or deflect away from the cannula point rather than enter the interior of the cannula and be captured.

The needle point of a typical biopsy cannula 10 is shown in prior art FIG. 1. The distal end 12 of the cylindrical cannula 10 is ground in a single plane P which lies at an angle α relative to the longitudinal axis 14 of the cannula 10. This produces an elliptical opening 16 at the distal end 12 of the cannula 10. The opening 16 is defined by the side wall 18 of the cannula 10 and provides an entrance to the lumen 20 of the cannula 10. The most distal portion of the side wall 18 forms the cutting edge 22. By choosing an appropriate angle α, e.g. 20°, the cutting edge 22 can be made very sharp. As shown in FIG. 1a, when the distal end 12 of the cannula 10 is advanced into target tissue 28, the tissue 28 is severed by the cutting edge 22 and follows a path relative to the opening 16 as shown by the arrow 24 in FIG. 1. Ideally, the tissue enters the opening 16, but depending on the properties of the tissue 28, the thickness of the sidewall 18, and the angle α, the tissue may merely be deflected away from the opening 16. Since the sharpest part of the cannula is the relatively small cutting edge 22, it is possible that the severed tissue will be guided by the sidewall 18 along a path lying in the plane P and never enter the opening 16.

SUMMARY OF THE INVENTION

It is therefore an object of the invention to provide a tissue core biopsy cannula having a sharp distal end.

It is also an object of the invention to provide a tissue core biopsy cannula having a distal end geometry which encourages the entry of target tissue into the cannula.

It is another object of the invention to provide a tissue core biopsy cannula having a larger cutting edge.

It is also an object of the invention to provide a tissue core biopsy cannula which holds a captured tissue sample securely while the cannula is withdrawn from target tissue.

In accord with these objects which will be discussed in detail below, the tissue core biopsy cannula of the present invention includes a distal end which is ground in two planes which intersect each other at a first angle along a line which intersects the longitudinal axis of the cannula at a second angle. This produces a cardioid shaped opening in the distal end of the cannula. The entire edge of the sidewall is inclined inward toward the distal opening and two distal cutting edges are provided. According to the presently preferred embodiment, the first angle at which the two grinding planes intersect is approximately 60° and the second angle at which the intersection of the two planes intersects the longitudinal axis of the cannula is approximately 20°. The provided cannula with the double cutting edge and the inclined sidewalls improves the cutting action as well as improving the likelihood that a sample will be captured.

In accord with other aspects of the invention, in order to aid in the capture and removal of the biopsy sample from the target tissue site, the cannula may be provided with side fenestration holes and/or a split end which aids in grasping the tissue, as the tissue prolapses into the holes or split. These features therefore permit the obtained core sample to be more readily pulled away from the target tissue site. In addition, the cannula according to the invention may be provided as part of a manual or automatic biopsy tool. Additional objects and advantages of the invention will become apparent to those skilled in the art upon reference to the detailed description taken in conjunction with the provided figures.

DETAILED DESCRIPTION OF THE PREFERRED EMBODIMENTS

Figure 2:
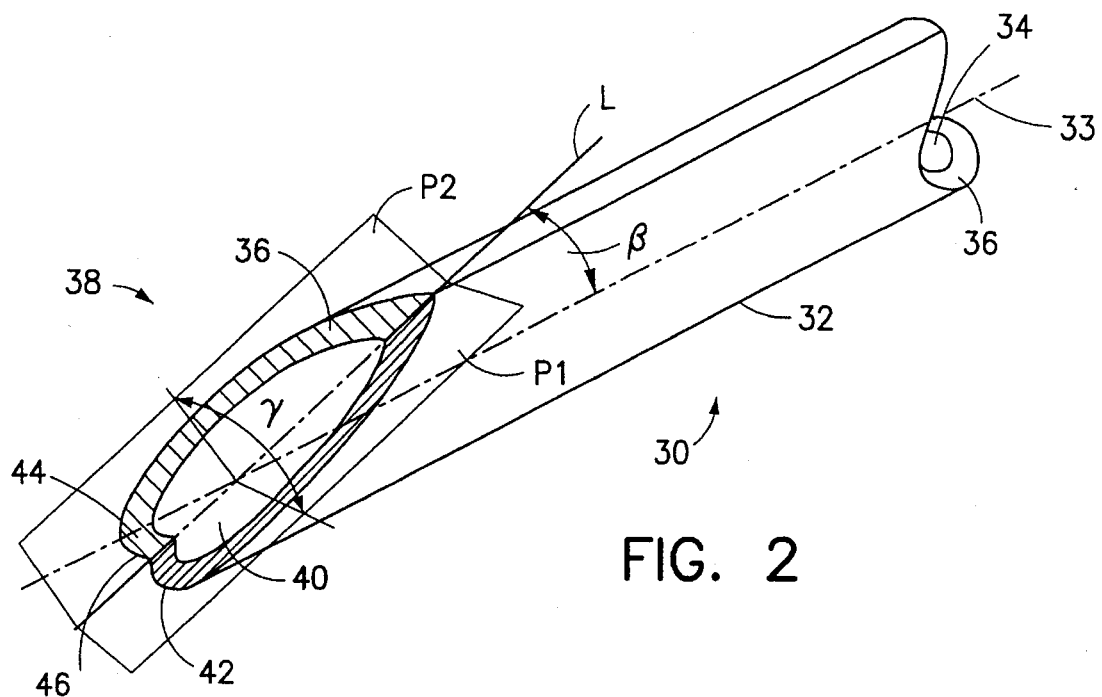
FIG. 2 is a broken perspective view of the distal end of a tissue core biopsy cannula according to the invention.
Figure 3:
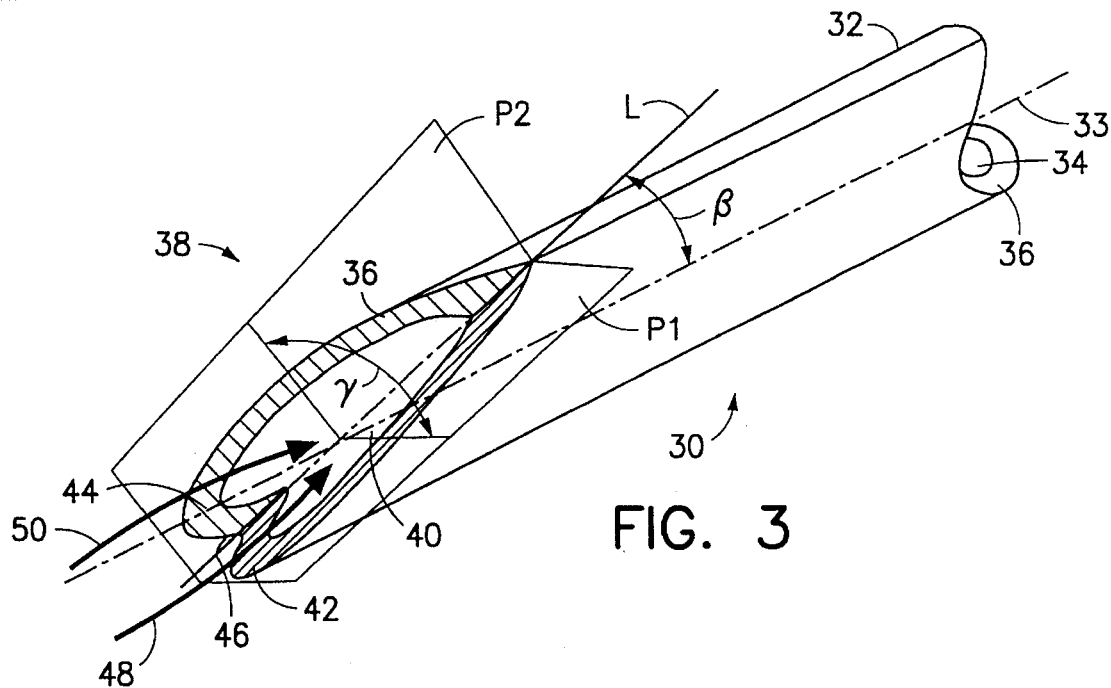
FIG. 3 is a broken perspective view of the distal end of an embodiment of a tissue core biopsy cannula according to the invention having the presently preferred angular dimensions.

Referring now to FIGS. 2 and 3, a tissue core biopsy cannula 30 according to the invention is a substantially cylindrical tube member 32 having a longitudinal axis 33 and a central lumen 34 defined by an inner wall 36. Opposite halves of the distal end 38 of the tube member 32 are ground in respective planes P1 and P2 such that the opening 40 to the lumen 34 assumes the shape of a cardioid. The planes P1 and P2 are chosen so that the intersect each other along a line L which forms an acute angle β with the longitudinal axis 33 of the tube member 32. In addition, the planes P1 and P2 form an angle γ between each other which is less than 180°. Thus, the side wall 36 at the distal end 38 of the tube member 32 is inclined inward toward the opening 40 and two cutting edges 42, 44 are formed at the distal end of the cannula 30. Moreover, a sharp narrow valley 46 is formed between the cutting edges 42, 44.

Figure 3A:
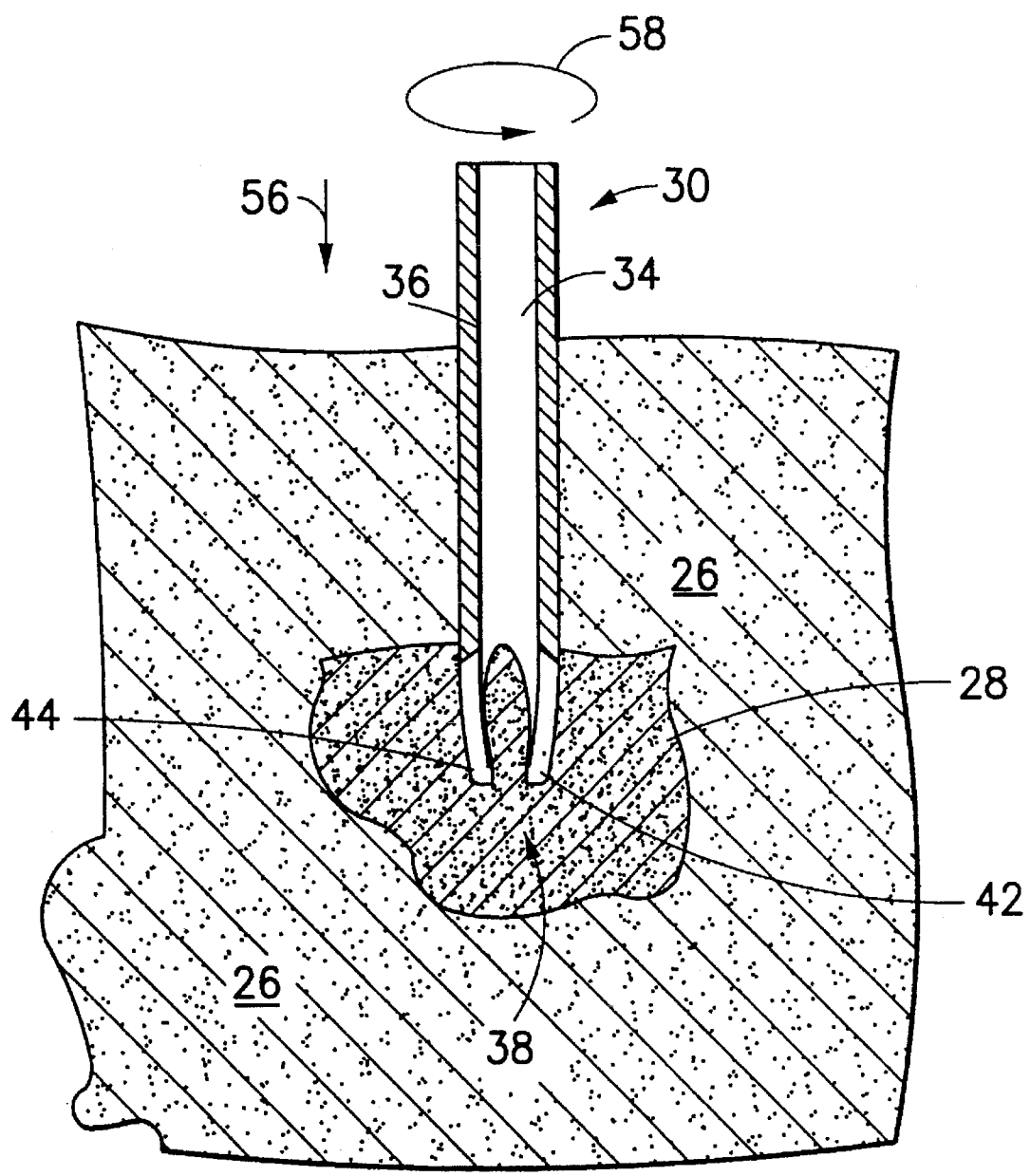
FIG. 3a is a broken longitudinal cross sectional view of the tissue core biopsy cannula of FIG. 3 advanced into a target tissue.

According to the presently preferred embodiment of the invention, shown in FIG. 3, the angle β is approximately 20° and the angle γ is approximately 60°. With this configuration, as the tissue sample is severed by the two cutting edges 42, 44, it is scooped into the opening 40 and flows into the lumen 34 as shown by the arrows 48 and 50. In comparing FIGS. 1a and 3a, it will be appreciated that the geometry of the distal end 38 of the cannula 30 of the invention guides the target tissue 28 through the opening 40 and into the lumen 34, and is more likely to assure that a sample is obtained.

Figure 1:
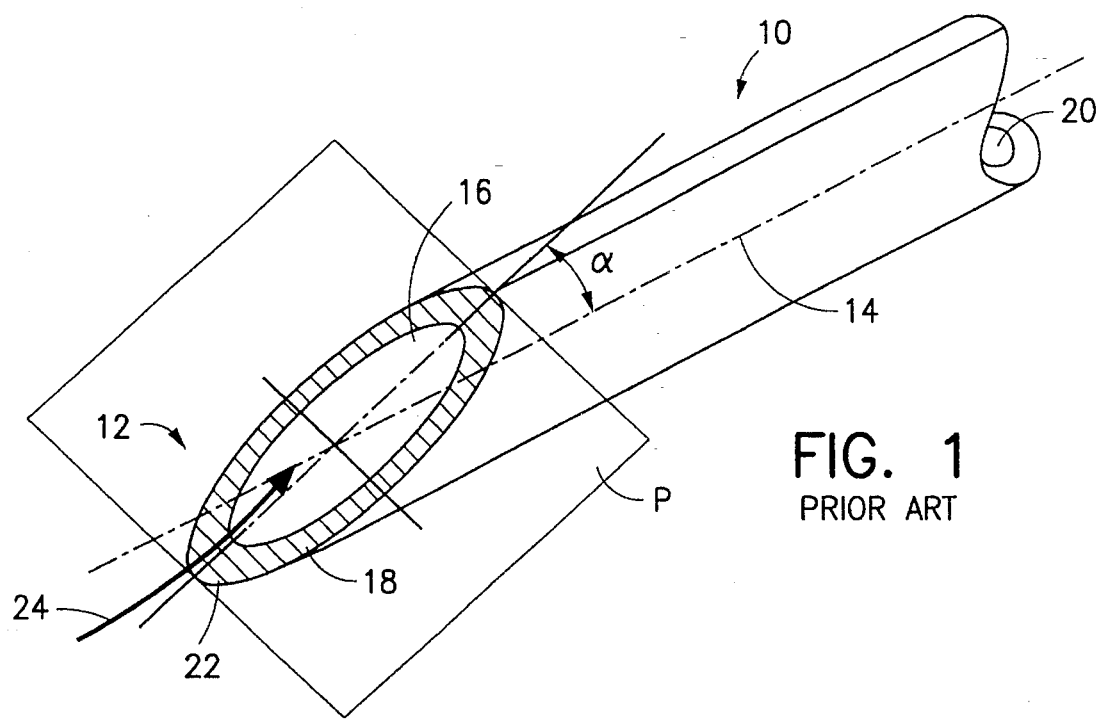
FIG. 1 is a broken perspective view of the distal end of a prior art tissue core biopsy cannula.
Figure 1A:
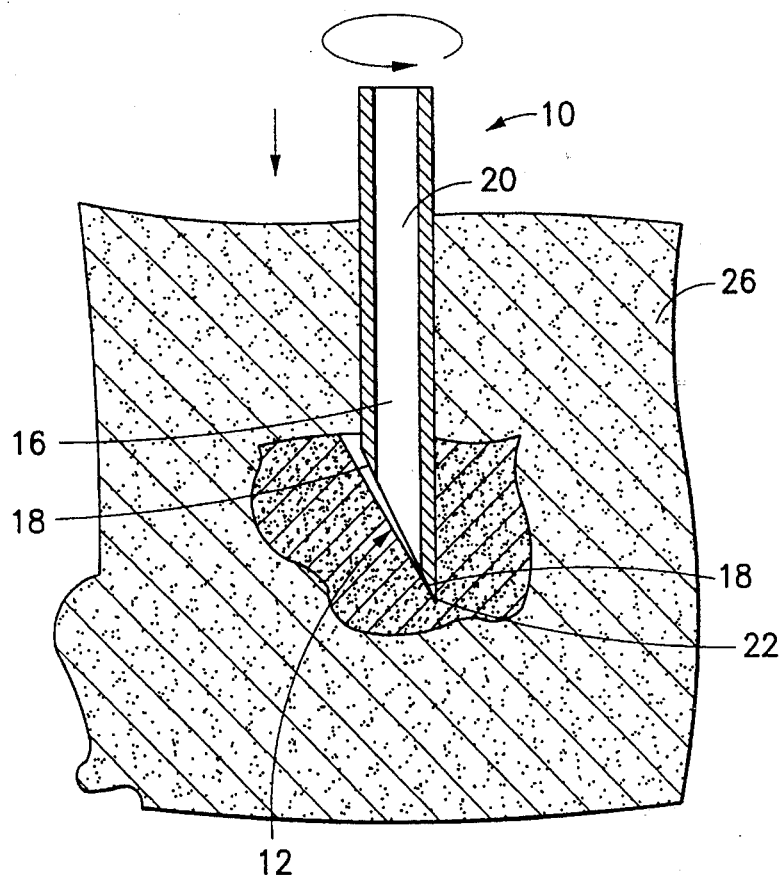
FIG. 1a is a broken longitudinal cross sectional view of the prior art tissue core biopsy cannula of FIG. 1 advanced into a target tissue.
Figure 4:
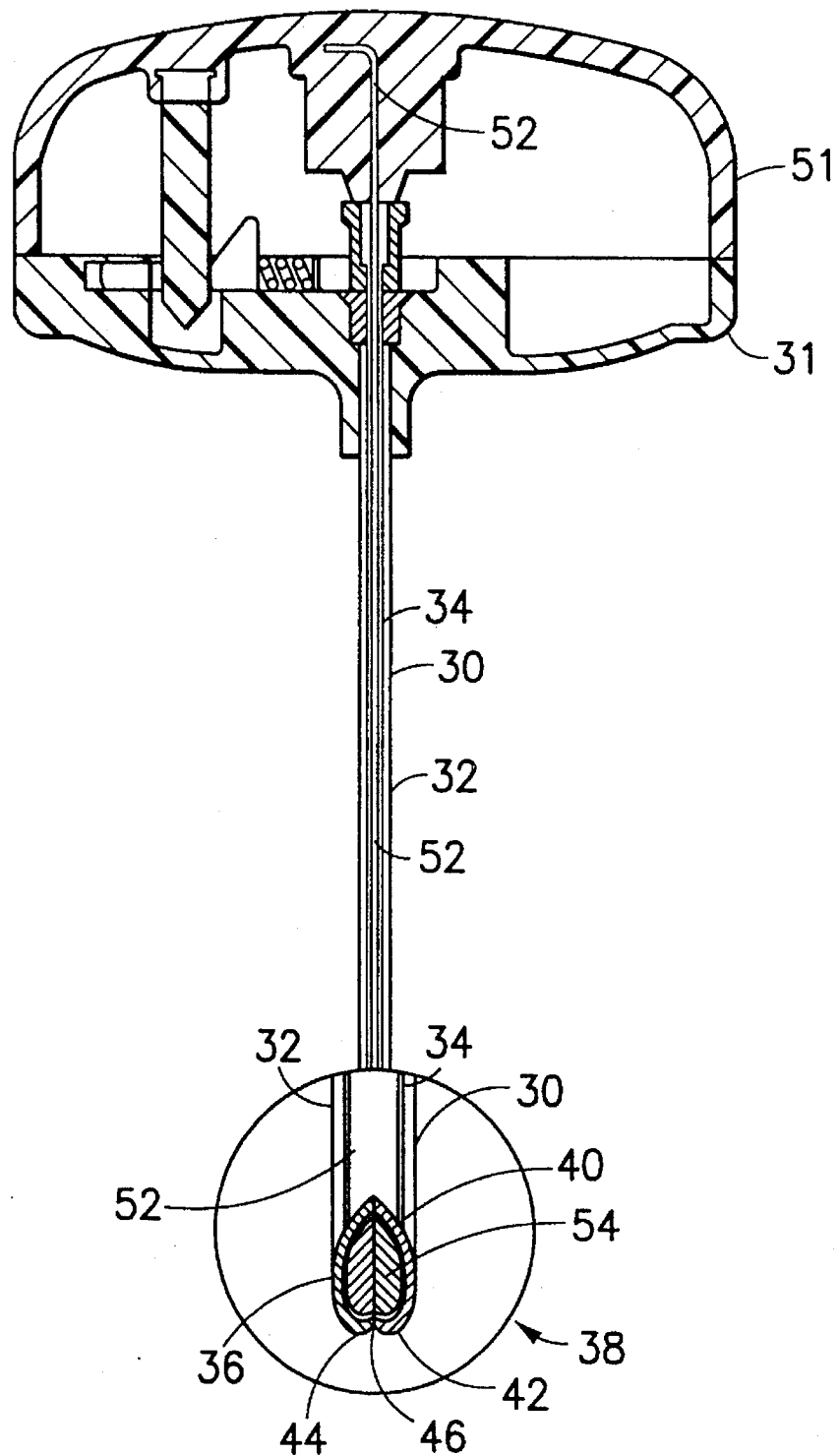
FIG. 4 is a partially transparent side elevation view in partial section with an enlarged portion showing the cannula according to FIG. 3 with a handle and an inserted stylet.

As mentioned above, and as seen in FIG. 3a and prior art FIG. 1a, the target tissue 28 is typically surrounded by other tissue 26 which is desirably not sampled. In order to prevent the surrounding tissue 26 from being inadvertently sampled during the biopsy procedure, a stylet is used in conjunction with the cannula. FIG. 4 shows the cannula 30 according to the invention with a handle 31 and an inserted stylet 52. The stylet 52 has a proximal handle 51, and is also provided with a distal tip 54 which is preferably ground in two planes like the distal end 38 of the cannula 30. In addition, the stylet 52 is preferably dimensioned so that the distal opening 40 to the lumen 34 is substantially completely occluded when the stylet is inserted as shown. In use, the cannula 30 and stylet 52 assembly is advanced through the surrounding tissue 26 (FIG. 3a) in the direction shown by the arrow 56. When the assembly reaches the target tissue 28, the stylet 52 is removed and the cannula 30 is advanced further into the target tissue 26. Rotation of the cannula 30 in a direction as shown by the arrow 58 aids in severing the sample from the target tissue 26.

Figure 5:
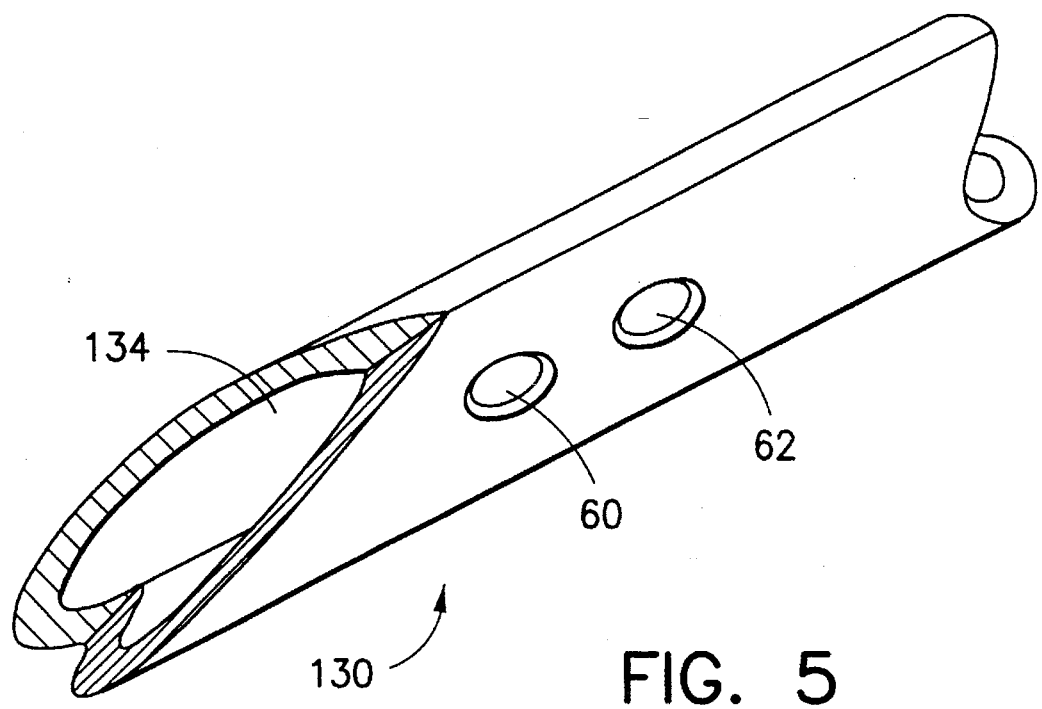
FIG. 5 is a view similar to FIG. 3 showing an embodiment of the invention having side fenestration holes.

Another embodiment of the invention is shown in FIG. 5. The cannula 130 shown in FIG. 5 is substantially the same as the cannula 30 shown and described above except for the addition of side fenestration holes 60, 62. The fenestration holes 60, 62 aid in securing the biopsy sample inside the lumen 134 of the cannula particularly during withdrawal of the cannula from the target tissue site. When the core sample tissue enters the lumen 134, it prolapses into the fenestration holes 60, 62 which hinders distal movement of the core sample out of the lumen 134. The cannula 130 shown in FIG. 5 may be used with or without a stylet.

Figure 6:
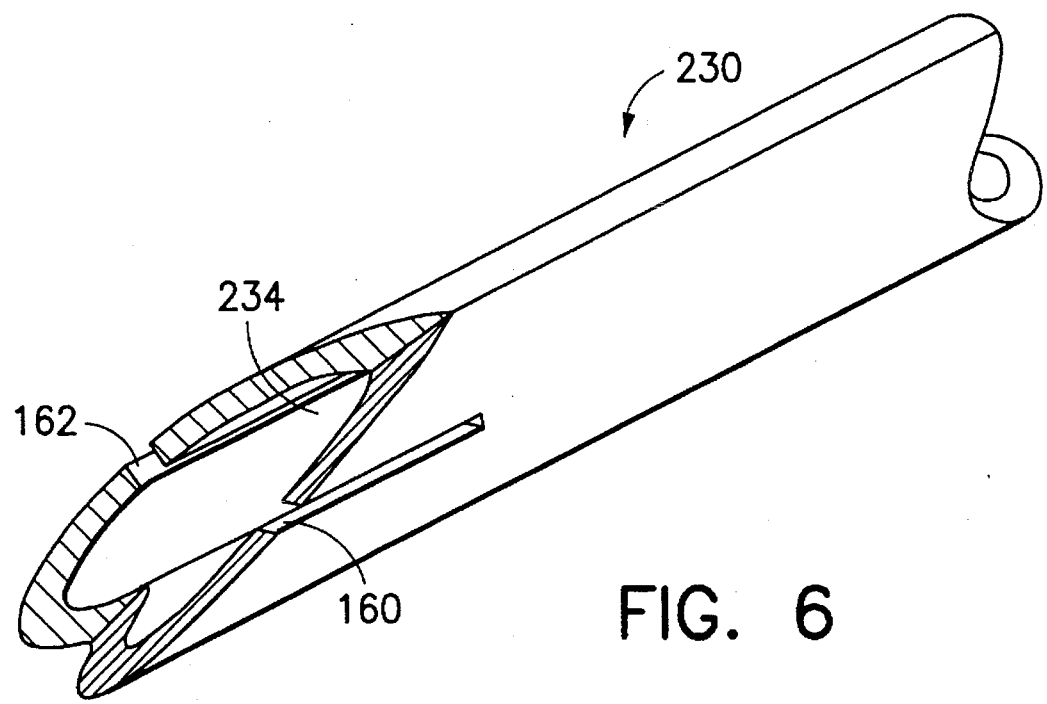
FIG. 6 is a view similar to FIG. 3 showing an embodiment of the invention having a split distal end.

Yet another embodiment of the invention is shown in FIG. 6. The cannula 230 shown in FIG. 6 is substantially the same as the cannula 30 shown and described above except for the addition of side slits 160, 162. The side slits 160, 162 aid in securing the biopsy sample inside the lumen 234 of the cannula during withdrawal of the cannula from the target tissue site. When the core sample tissue enters the lumen 234, lateral portions of the sample tissue extend outward from the side slits. When the cannula 230 is rotated, the tissue is torn at the side slits of the cannula. The cannula 230 shown in FIG. 6 may be used with or without a stylet.

There have been described and illustrated herein several embodiments of a tissue core biopsy cannula. While particular embodiments of the invention have been described, it is not intended that the invention be limited thereto, as it is intended that the invention be as broad in scope as the art will allow and that the specification be read likewise. Thus, while particular preferred surface angles have been disclosed, it will be appreciated that other angles could be utilized. Also, while the cannula has been shown as a substantially cylindrical member, it will be recognized that a non-cylindrical member could be used with similar results obtained. Moreover, while particular configurations have been disclosed in reference to fenestration holes and side slits, it will be appreciated that other configurations could be used as well. It will therefore be appreciated by those skilled in the art that yet other modifications could be made to the provided invention without deviating from its spirit and scope as so claimed.

We claim:

1. A tissue core biopsy cannula, comprising:

a tube member defining a lumen, said tube member having a longitudinal axis and a distal end, said lumen extending proximally from said distal end, said distal end lying in two planes which intersect each other at a first angle along a line, with said line intersecting said longitudinal axis at a second angle.

2. A tissue core biopsy cannula according to claim 1, wherein:

said distal end of said tube member has an opening with a cardioid shape.

3. A tissue core biopsy cannula according to claim 1, wherein:

said first angle is acute.

4. A tissue core biopsy cannula according to claim 1, wherein:

said first angle is approximately sixty degrees and said second angle is approximately twenty degrees.

5. A tissue core biopsy cannula according to claim 1, wherein:

said tube member is provided with at least one fenestration hole near said distal end.

6. A tissue core biopsy cannula according to claim 1, wherein:

said distal end of said tube member has a longitudinal slit.

7. A tissue core biopsy cannula according to claim 1, wherein:

said tube member is substantially cylindrical.

8. A tissue core biopsy cannula according to claim 1, wherein:

said lumen is substantially cylindrical.

9. A tissue core biopsy cannula according to claim 4, wherein:

said tube member is provided with at least one fenestration hole near said distal end.

10. A tissue core biopsy cannula according to claim 4, wherein:

said distal end of said tube member has a longitudinal slit.

11. A tissue core biopsy cannula according to claim 4, wherein:

said tube member is substantially cylindrical.

12. A tissue core biopsy cannula according to claim 4, wherein:

said lumen is substantially cylindrical.

13. A tissue core biopsy cannula according to claim 11, wherein:

said tube member is provided with at least one fenestration hole near said distal end.

14. A tissue core biopsy cannula according to claim 11, wherein:

said distal end of said tube member has a longitudinal slit.

15. A tissue core biopsy instrument comprising:

a) a cannula having a proximal end and a distal end with a lumen extending therethrough; and b) a handle coupled to said proximal end of said cannula, wherein said cannula has a longitudinal axis and said distal end of said cannula lies in two planes which intersect each other at a first angle along a line, with said line intersecting said longitudinal axis at a second angle.

16. A tissue core biopsy instrument according to claim 15, wherein:

said first angle is approximately sixty degrees and said second angle is approximately twenty degrees.

17. A tissue core biopsy instrument according to claim 15, wherein:

said cannula is provided with at least one fenestration hole near said distal end.

18. A tissue core biopsy instrument according to claim 15, wherein:

said distal end of said cannula has a longitudinal slit.

19. A tissue core biopsy instrument according to claim 15, further comprising:

c) a stylet having a proximal end and a distal end; and d) a stylet handle coupled to said proximal end of said stylet, wherein said stylet is dimensioned such that it is insertable into said lumen, extends through substantially all of said lumen, and substantially occludes the distal end of said lumen.

20. A tissue core biopsy instrument according to claim 19, wherein:

said stylet has a longitudinal axis and said distal end of said stylet lies in two planes which intersect each other at a third angle along a line, with said line intersecting said longitudinal axis at a fourth angle, said third angle being substantially equal to said first angle, and said fourth angle being substantially equal to said second angle.

* * * * *